(12) United States Patent
Otto et al.

(10) Patent No.: US 9,623,247 B2
(45) Date of Patent: Apr. 18, 2017

(54) NEUROMODULATORY METHOD FOR TREATING CHRONIC OR REFRACTORY RHINITIS

(71) Applicant: The Ohio State University, Columbus, OH (US)

(72) Inventors: Bradley A Otto, Columbus, OH (US); Ali R Rezai, Columbus, OH (US)

(73) Assignee: The Ohio State University, Columbus, OH (US)

( * ) Notice: Subject to any disclaimer, the term of this patent is extended or adjusted under 35 U.S.C. 154(b) by 459 days.

(21) Appl. No.: 13/864,491

(22) Filed: Apr. 17, 2013

(65) Prior Publication Data

US 2013/0274831 A1 Oct. 17, 2013

Related U.S. Application Data

(60) Provisional application No. 61/625,374, filed on Apr. 17, 2012.

(51) Int. Cl.
*A61N 1/00* (2006.01)
*A61N 1/36* (2006.01)
*A61N 1/05* (2006.01)

(52) U.S. Cl.
CPC ........... *A61N 1/36135* (2013.01); *A61N 1/05* (2013.01); *A61N 1/3606* (2013.01); *A61N 1/36139* (2013.01); *A61N 1/3605* (2013.01); *A61N 1/36053* (2013.01)

(58) Field of Classification Search
CPC ... A61N 1/00; A61N 1/02; A61N 1/04; A61N 1/05; A61N 1/06; A61N 1/08; A61N 1/18; A61N 1/40
See application file for complete search history.

(56) References Cited

U.S. PATENT DOCUMENTS

2010/0185258 A1 7/2010 Papay
2011/0276107 A1 11/2011 Simon et al.

FOREIGN PATENT DOCUMENTS

WO 2008150963 12/2008

*Primary Examiner* — Christopher D Koharski
*Assistant Examiner* — Elizabeth K So
(74) *Attorney, Agent, or Firm* — Tarolli, Sundheim, Covell & Tummino LLP

(57) ABSTRACT

One aspect of the present disclosure includes a method for treating chronic or refractory rhinitis in a subject. One step of the method includes implanting a therapy delivery system in the subject so that at least one therapy delivery component of the system is positioned substantially adjacent a target location where modulation of the autonomic nervous system (ANS) is effective to treat chronic or refractory rhinitis. The therapy delivery component includes at least one electrode configured to deliver electric current to the target location. Next, electric current is delivered to the at least one electrode to effect a change in the ANS.

11 Claims, 6 Drawing Sheets

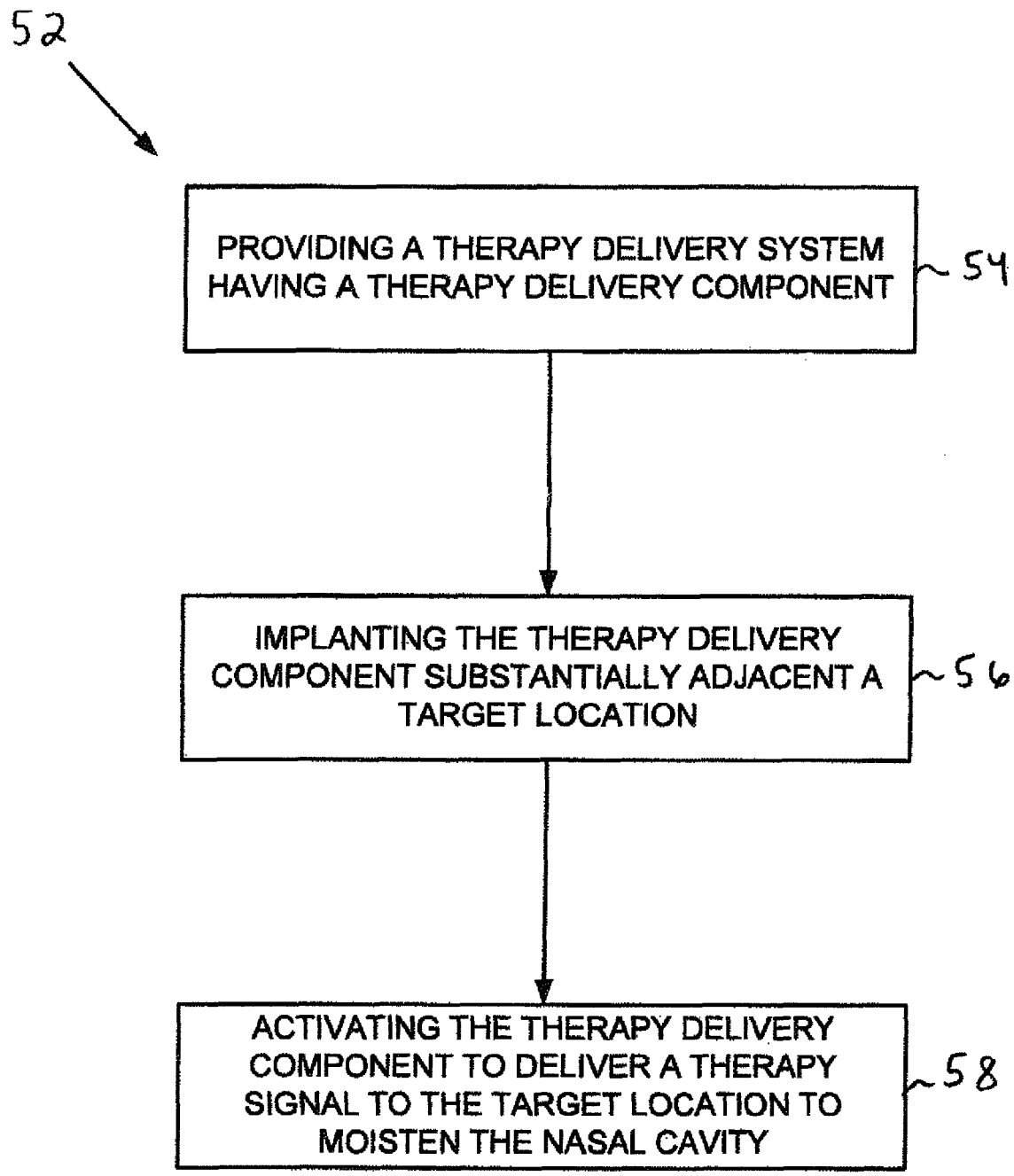

NEUROMODULATORY METHOD FOR TREATING CHRONIC OR REFRACTORY RHINITIS

RELATED APPLICATION

This application claims the benefit of U.S. Provisional Patent Application Ser. No. 61/625,374, filed Apr. 17, 2012, the entirety of which is hereby incorporated by reference for all purposes.

TECHNICAL FIELD

The present disclosure relates to a neuromodulatory method for treating inflammation of the nasal passages, and in particular to a method of treating chronic or refractory rhinitis by modulation of the autonomic nervous system.

BACKGROUND

Rhinitis is an inflammatory state of the nasal passages that is generally characterized by symptoms such as nasal drainage, nasal itching, sneezing, and/or nasal congestion. Acute rhinitis, such as that associated with viral upper respiratory infections, generally resolves after immunological clearance of the offending organism. Conversely, patients with chronic rhinitis tend to have a clinical course characterized by long-term persistent or recurrent symptoms. Affecting nearly one quarter of Westernized populations, rhinitis has been shown to have a significant impact on overall health and productivity. Rhinitis has shown to be a possible predictor of future asthma in children. Rhinitis also contributes to poor school and work performance.

Chronic rhinitis is broadly organized into allergic and non-allergic forms. Traditionally, allergic rhinitis has been categorized as either seasonal or perennial. However, since many patients are sensitive to both seasonal and perennial allergens, this categorization is being challenged. A newer categorization based on the timeline (intermittent or persistent) and severity (mild or moderate/severe) of symptoms is increasingly used. The treatment for allergic rhinitis depends on the severity and persistence of symptoms. The mainstay of medical therapy includes one or more of the following and is titrated to the patient's response and tolerance: antihistamines; steroids; leukotriene receptor antagonists; leukotriene synthesis inhibitors; mast cell stabilizers; anticholinergic drugs; and monoclonal antibody therapy.

Avoidance of offending pollens or foods is also a mainstay of therapy. For those patients who fail cannot tolerate medical therapy, allergy immunotherapy is offered as a treatment alternative. Although immunotherapy can be quite effective, it may take years of weekly treatments (subcutaneous shots), usually performed at the treating physician's office, to achieve long-term efficacy. Furthermore, many patients with significant symptoms (up to 25%) remain symptomatic despite ongoing immunotherapy.

Non-allergic rhinitis (NAR) is similar to allergic rhinitis, although ocular symptoms such as redness, itching or tearing are less common in NAR. Classification of NAR is simple, as there are many subtypes of NAR, both inflammatory and non-inflammatory. Inflammatory non-allergic rhinitis may be associated with occupational exposure, drugs (including prescription and over-the-counter), infection, and NAR with eosinophilia syndrome. Non-inflammatory NAR may be one of the following forms: emotional; idiopathic; atrophic; gustatory; vasomotor; hormonal; or drug related (such as rhinitis medicamentosa). Treatment is aimed at addressing the offending etiological factor (such as stopping the use of topical decongestants for patients with rhinitis medicamentosa). In select cases, steroids, antibiotics, anticholinergics, or other medications as noted for allergic rhinitis may be of benefit. However, for many NAR patients, there exists no optimal or effective treatment.

SUMMARY

One aspect of the present disclosure includes a method for treating chronic or refractory rhinitis in a subject. One step of the method includes implanting a therapy delivery system in the subject so that at least one therapy delivery component of the system is positioned substantially adjacent a target location where modulation of the autonomic nervous system (ANS) is effective to treat chronic or refractory rhinitis. The therapy delivery component includes at least one electrode configured to deliver electric current to the target location. Next, electric current is delivered to the at least one electrode to effect a change in the ANS.

Another aspect of the present disclosure includes a method for treating chronic or refractory rhinitis. One step of the method includes implanting a closed-loop therapy delivery system in the subject so that at least one therapy delivery component of the system is positioned substantially adjacent a target location where modulation of the ANS is effective to treat chronic or refractory rhinitis. The therapy delivery component includes at least one electrode configured to deliver electric current to the target location. Next, electric current is delivered to the at least one electrode to effect a change in the ANS. At least one physiological parameter associated with chronic or refractory rhinitis is then sensed by the therapy delivery system. The therapy delivery component of the system is activated to adjust application of electric current to the target site in response to the sensed at least one physiological parameter.

Another aspect of the present disclosure includes a method for moistening a nasal passage of a subject. One step of the method includes implanting a therapy delivery system in the subject so that at least one therapy delivery component of the system is positioned substantially adjacent a target location where modulation of the ANS is effective to moisten the nasal passage. The therapy delivery component includes at least one electrode configured to deliver electric current to the target location. Next, electric current is delivered to the at least one electrode to effect a change in the ANS.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 6 is a process flow diagram illustrating a method for moistening a nasal passage of a subject according to another aspect of the present disclosure.

DETAILED DESCRIPTION

Figure 1:
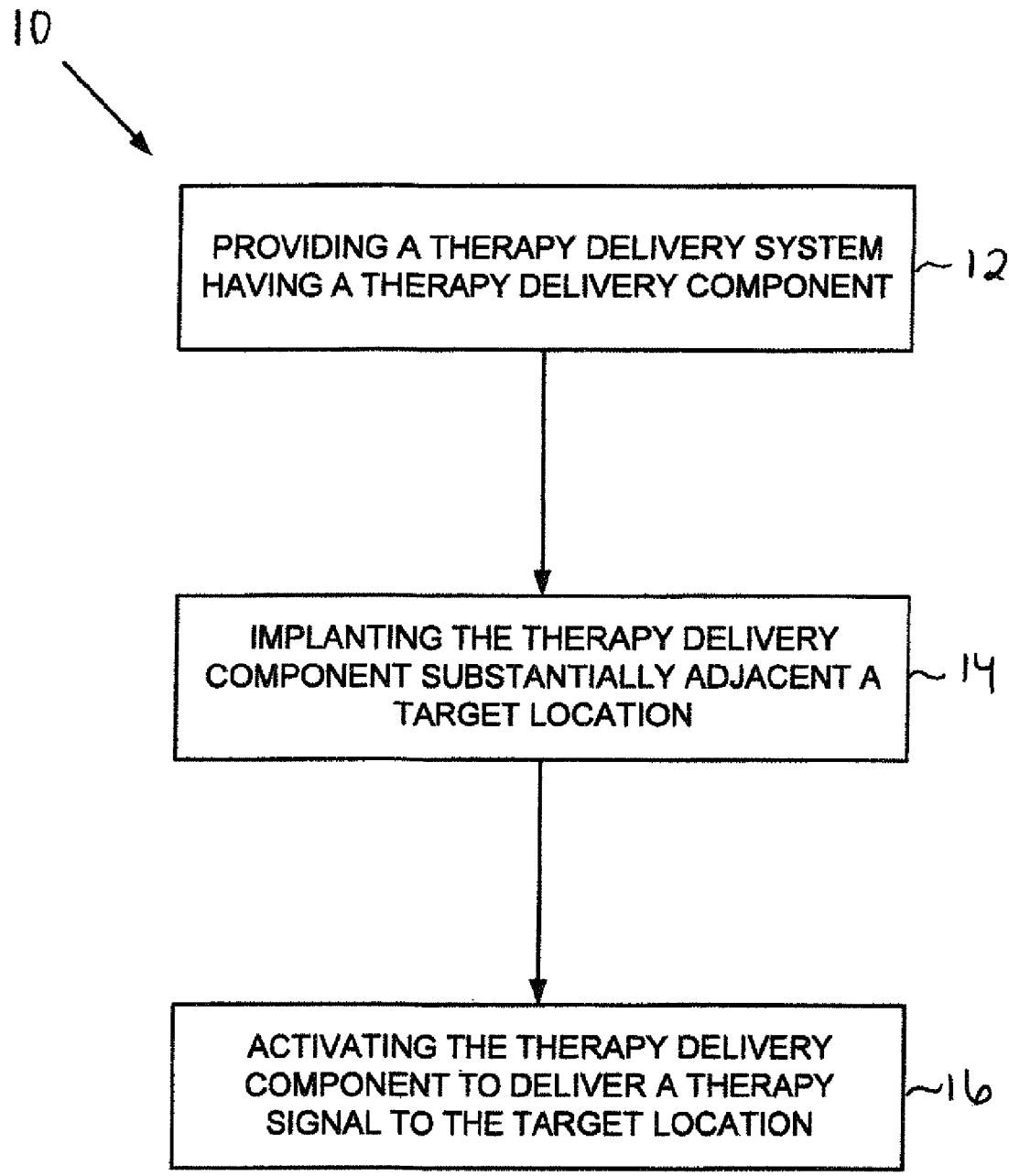
FIG. 1 is a process flow diagram illustrating a method for treating chronic or refractory rhinitis according to one aspect of the present disclosure.

The present disclosure relates to a neuromodulatory method for treating inflammation of the nasal passages, and in particular to a method of treating chronic or refractory rhinitis by modulation of the autonomic nervous system (ANS). As representative of one aspect of the present disclosure, FIG. 1 illustrates a method 10 for treating chronic or refractory rhinitis in a subject. The present disclosure addresses physiologic changes and symptoms associated with chronic or refractory rhinitis by focusing treatment on the ANS and, in particular, nerve structures or nervous tissue associated with the pterygopalatine fossa (PPF) 18 (FIG. 2) to modulate the neurovascular contribution to nasal immunity and physiology. As described in more detail below, the present disclosure can deliver therapy either on-demand or continuously in a dynamic fashion. Consequently, therapy can be titrated based on real-time conditions and symptoms associated with chronic or refractory rhinitis.

Unless otherwise defined, all technical terms used herein have the same meaning as commonly understood by one of ordinary skill in the art to which the present disclosure pertains.

In the context of the present disclosure, the terms "nervous tissue" and "nerve structure" can refer to any tissues of the ANS including, but not limited to, neurons, axons, fibers, tracts, nerves, plexus, afferent plexus fibers, efferent plexus fibers, ganglion, pre-ganglionic fibers, post-ganglionic fibers, cervical sympathetic ganglia/ganglion, thoracic sympathetic ganglia/ganglion, afferents, efferents, and combinations thereof.

As used herein, the terms "modulate" or "modulating" can refer to causing a change in neuronal activity, chemistry, and/or metabolism. The change can refer to an increase, decrease, or even a change in a pattern of neuronal activity. The terms may refer to either excitatory or inhibitory stimulation, or a combination thereof, and may be at least electrical, magnetic, optical or chemical, or a combination of two or more of these. The terms "modulate" or "modulating" can also be used to refer to a masking, altering, overriding, or restoring of neuronal activity.

As used herein, the term "rhinitis" can refer to any disorder of the nose in which there is inflammation of the nasal mucosal lining by one or more causes (e.g., intrinsic, extrinsic, allergic, non-allergic, or combinations thereof).

As used herein, the term "chronic rhinitis" can refer to irritation and inflammation of some internal area(s) of the nasal cavity that result in at least rhinorrhea (e.g., profuse water discharge, excess mucous production), and possibly one or more additional symptoms (discussed below). The term can also refer to irritation and inflammation of some internal area(s) of the nasal cavity that: (1) persists for more than about four days per week; or (2) persists for more than about four weeks.

As used herein, the term "refractory rhinitis" can refer to any form of rhinitis (e.g., chronic rhinitis) for which conventional therapies are not therapeutically effective to relieve, alleviate, prevent, mitigate or block one or more symptoms thereof.

As used herein, the term "target location" can refer to a suitable anatomical location at which a therapy delivery system, and in particular a therapy delivery component of the system, may be positioned to effect a chance in the ANS. In some instances, the target location can comprise an anatomical location that is innervated by, or in electrical communication with, one or more autonomic and/or sensory nerves extending, or involved in the interplay, between the sinonasal cavity and the PPF. In other instances, the target location can comprise a variety of anatomical locations, including intraluminal and extraluminal locations innervated by, or in electrical communication with, a nerve structure or nervous tissue associated with the PPF, such as a nerve structure or nervous tissue of the ANS. Other target locations and associated nerve structures or nervous tissue contemplated by the present disclosure are described in further detail below.

As used herein, the term "electrical communication" can refer to the ability of an electric field generated by an electrode (or electrode array) to be transferred, or to have a neuromodulatory effect, within and/or on at least one nerve, neuron, nerve structure and/or nervous tissue of the ANS.

As used herein, the term "subject" can refer to any warm-blooded organism including, but not limited to, human beings, pigs, rats, mice, dogs, goats, sheep, horses, monkeys, apes, rabbits, cattle, etc.

As used herein, the terms "treating" and "treat" can refer to therapeutically regulating, preventing, improving, alleviating the symptoms of, and/or reducing the effects or symptoms of chronic or refractory rhinitis. The terms can also refer to chronic or acute treatment.

As used herein, the term "therapy signal" can refer to an electrical and/or chemical signal that is delivered to a target location and is capable of modulating (e.g., electrically modulating) a nerve structure or nervous tissue to effect a change in the ANS.

When an element or structure is referred to as being "on," "engaged to," "connected to," or "coupled to" another element or structure, it may be directly on, engaged, connected or coupled to the other element or structure, or intervening elements or structures may be present. In contrast, when an element is referred to as being "directly on," "directly engaged to," "directly connected to," or "directly coupled to" another element or structure, there may be no intervening elements or structures present. Other words used to describe the relationship between elements should be interpreted in a like fashion (e.g., "between" versus "directly between," "adjacent" versus "directly adjacent," etc.).

A brief discussion of the neurophysiology is provided to assist the reader with understanding the present disclosure. The nervous system is divided into the somatic nervous system and the ANS. In general, the somatic nervous system controls organs under voluntary control (e.g., skeletal muscles) and the ANS controls individual organ function and homeostasis. For the most part, the ANS is not subject to voluntary control. The ANS is also referred to as the visceral or automatic system.

The ANS can be viewed as a "real-time" regulator of physiological functions that extracts features from the environment and, based on that information, allocates an organism's internal resources to perform physiological functions for the benefit of the organism, e.g., responds to environment conditions in a manner that is advantageous to the organism.

The ANS conveys sensory impulses to and from the central nervous system to various structures of the body such as organs and blood vessels, in addition to conveying sensory impulses through reflex arcs. For example, the ANS controls: constriction and dilatation of blood vessels; heart rate; the force of contraction of the heart; contraction and relaxation of smooth muscle in various organs; lungs; stomach; colon; bladder; and visual accommodation, secretions from exocrine and endocrine glands, etc. The ANS does this through a series of nerve fibers, and more specifically through efferent and afferent nerves. The ANS acts through a balance of its two components: the sympathetic nervous system (SNS) and the parasympathetic nervous system (PNS), which are two anatomically and functionally distinct systems. Both of these systems include myelinated preganglionic fibers, which make synaptic connections with unmyelinated postganglionic fibers, and it is these fibers that then innervate the effector structure. These synapses usually occur in clusters called ganglia. Most organs are innervated by fibers from both divisions of the ANS, and the influence is usually opposing (e.g., the vagus nerve slows the heart, while the sympathetic nerves increase its rate and contractility), although it may be parallel (e.g., as in the case of the salivary glands). Each of these is briefly reviewed below.

The PNS is the part of the ANS controlling a variety of autonomic functions including, but not limited to, involuntary muscular movement of blood vessels and gut and glandular secretions from eye, salivary glands, bladder, rectum and genital organs. The vagus nerve is part of the PNS. Parasympathetic nerve fibers are contained within the last five cranial nerves and the last three spinal nerves and terminate at parasympathetic ganglia near or in the organ they supply. The actions of the PNS are broadly antagonistic to those of the SNS; lowering blood pressure, slowing heartbeat, stimulating the process of digestion etc. The chief neurotransmitter in the PNS is acetylcholine. Neurons of the parasympathetic nervous system emerge from the brainstem as part of the Cranial nerves III, VII, IX and X (vagus nerve) and also from the sacral region of the spinal cord via Sacral nerves. Because of these origins, the PNS is often referred to as the "craniosacral outflow".

In the PNS, both pre- and post-ganglionic neurons are cholinergic (i.e., they utilize the neurotransmitter acetylcholine). Unlike adrenaline and noradrenaline, which the body takes around 90 minutes to metabolize, acetylcholine is rapidly broken down after release by the enzyme cholinesterase. As a result the effects are relatively brief in comparison to the SNS.

Each pre-ganglionic parasympathetic neuron synapses with just a few post-ganglionic neurons, which are located near, or in, the effector organ, a muscle or gland. As noted above, the primary neurotransmitter in the PNS is acetylcholine such that acetylcholine is the neurotransmitter at all the pre-ganglionic neurons and many of the post-ganglionic neurons of the PNS. Some of the post-ganglionic neurons, however, release nitric oxide as their neurotransmitter.

The SNS is the part of the ANS comprising nerve fibers that leave the spinal cord in the thoracic and lumbar regions and supply viscera and blood vessels by way of a chain of sympathetic ganglia running on each side of the spinal column, which communicate with the central nervous system via a branch to a corresponding spinal nerve. The SNS controls a variety of autonomic functions including, but not limited to, control of movement and secretions from viscera and monitoring their physiological state, stimulation of the sympathetic system inducing, e.g., the contraction of gut sphincters, heart muscle and the muscle of artery walls, and the relaxation of gut smooth muscle and the circular muscles of the iris. The chief neurotransmitter in the SNS is adrenaline, which is liberated in the heart, visceral muscle, glands and internal vessels, with acetylcholine acting as a neurotransmitter at ganglionic synapses and at sympathetic terminals in skin and skeletal muscles. The actions of the SNS tend to be antagonistic to those of the PNS.

The neurotransmitter released by the post-ganglionic neurons is nonadrenaline (also called norepinephrine). The action of noradrenaline on a particular structure, such as a gland or muscle, is excitatory in some cases and inhibitory in others. At excitatory terminals, ATP may be released along with noradrenaline. Activation of the SNS may be characterized as general because a single pre-ganglionic neuron usually synapses with many post-ganglionic neurons, and the release of adrenaline from the adrenal medulla into the blood ensures that all the cells of the body will be exposed to sympathetic stimulation even if no post-ganglionic neurons reach them directly.

Figure 2:
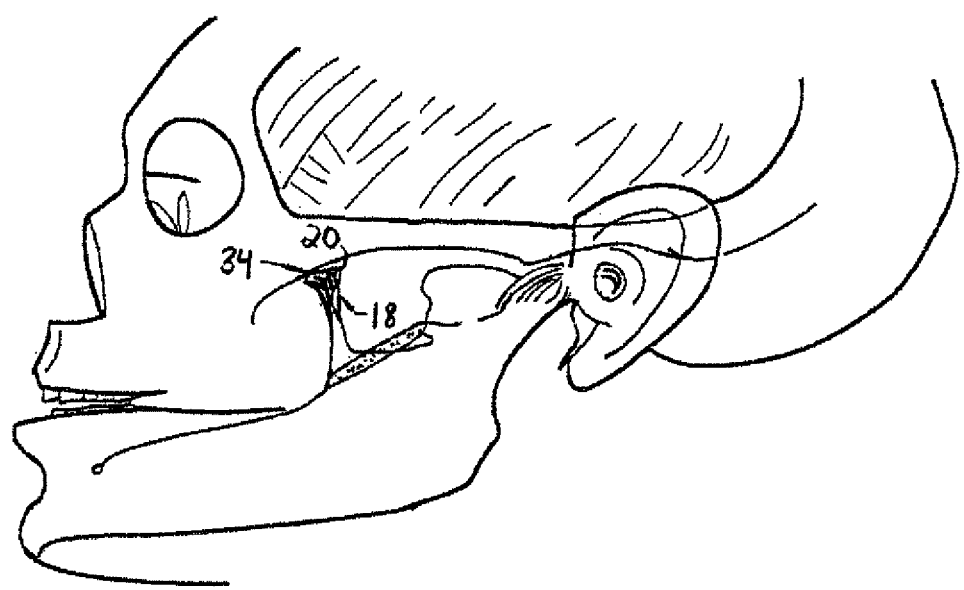
FIG. 2 is a is a schematic drawing of a lateral view of the skull showing the position of the infratemporal fossa with the sphenopalatine ganglion (SPG) lying within the sphenopalatine fossa, surrounded by the anterior margin of the lateral pterygoid plate and the posterior wall of the maxillary sinus.
Figure 3:
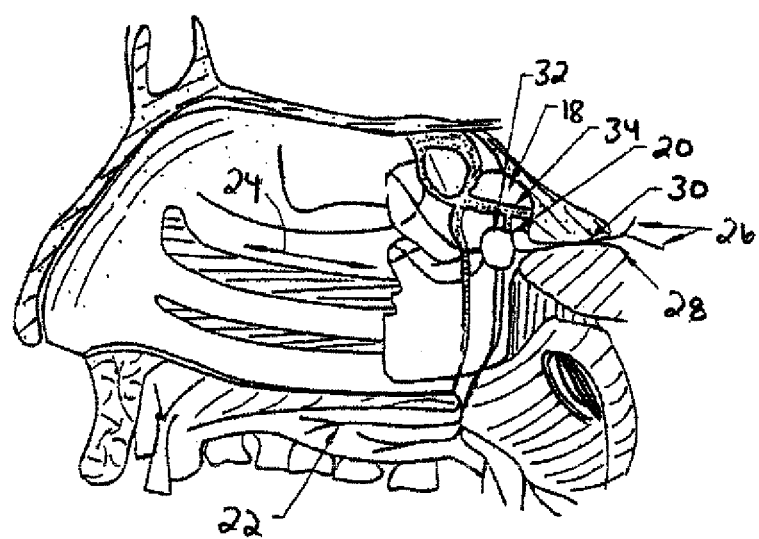
FIG. 3 is a schematic illustration of a lateral view of the lateral nasal wall showing the position of the SPG directly underneath the nasal mucosa and located at the posterior margin of the superior and middle nasal turbinates.

Referring to FIGS. 2-3, the sphenopalatine ganglion (SPG) 20 is located behind the maxilla 22 in the PPF 18 posterior to the middle nasal turbinate 24. The SPG 20 is surrounded by a layer of mucosal and connective tissue of less than five millimeters in thickness. The SPG 20 is part of the parasympathetic division of the ANS; however, the SPG has both sympathetic and parasympathetic nerve fibers, as well as sensory and visceral nerve fibers. The parasympathetic activity of the SPG 20 is mediated through the greater petrosal nerve 26, while the sympathetic activity of the SPG is mediated through the deep petrosal nerve 26, which is essentially an extension of the cervical sympathetic chain. Facial nerve and carotid plexuses directly communicate sensory signals to the SPG 20, and cell bodies in the ventral horn of the thoracolumbar spinal cord send fibers either directly or via cervical ganglion to the SPG.

The deep and greater petrosal nerves 26 join together just before entering the pterygoid canal to form the vidian nerve 28. The vidian nerve 28 is housed within the vidian canal 30, which is directly posterior to the SPG 20. The vidian nerve 28 connects to the SPG 20 and contains parasympathetic fibers, which synapse in the SPG, sensory fibers that provide sensation to part of the nasal septum, and also sympathetic fibers.

The sphenopalatine nerves 32 are sensory nerves that connect the SPG 20 to the maxillary nerve 34. The sphenopalatine nerves 32 traverse through the SPG 20 without synapsing and proceed to provide sensation to the palate. The sphenopalatine nerves 32 suspend the SPG 20 in the PPF.

Having described the relevant physiology and anatomy to which the present disclosure pertains, one aspect of the present disclosure can include a method 10 for treating chronic or refractory rhinitis in a subject. Referring to FIG. 1, the method 10 can include providing a therapy delivery system 36 having a therapy delivery component 38 (Step 12). At Step 14, the therapy delivery system 36 can be implanted in the subject so that at least one therapy delivery component 38 of the system is positioned substantially adjacent a target location where modulation of the ANS is effective to treat chronic or refractory rhinitis. As described in more detail below, the therapy delivery component 38 can include at least one electrode (not shown) configured to deliver a therapy signal, such as electric current to the target location. After appropriately positioning the therapy delivery system 36 (e.g., the therapy delivery component 38), the therapy signal can be delivered to the at least one electrode to effect a change in the ANS and thereby treat the chronic or refractory rhinitis (Step 16).

If left untreated, chronic rhinitis can lead to serious complications. For example, complications of untreated chronic rhinitis can include thickening of nasal epithelium and connective tissue proliferation (e.g., leading to loss of epithelial cilia), development of sinusitis, asthma development, asthma trigger (e.g., via post-nasal drip), otitis media with hearing loss, and laryngitis. Thus, one aspect of the present disclosure can include identifying a subject with chronic or refractory rhinitis. One skilled in the art will appreciate how to identify or diagnose a subject with chronic or refractory rhinitis. Generally, identification of a subject with chronic or refractory rhinitis can include examination of the nasal vault or passages, which includes examining the following: the quality of mucous secretions (e.g., amount, location and thickness); and the presence of purulence, blood or discoloration. A subject can also be examined for: edema of the nasal mucosa; sneezing; inflammation of the nasal mucosa; congestion; ulceration or excoriation; erosion; atrophy; red or watery eyes; blockage in the ears; headaches; fatigue; and if post-nasal drip is involved, the presence of a sore throat or chronic cough.

In one example, the subject can have a refractory or recalcitrant form of rhinitis (e.g., chronic rhinitis) in which symptoms persist despite medical or surgical treatment. In another example, the subject treatable by the present disclosure may have a form of rhinitis (e.g., chronic rhinitis) but be unable to receive standard medical or surgical care due to contraindications for such care.

After identifying a subject suffering from chronic or refractory rhinitis, another aspect of the present disclosure can include providing a therapy delivery system 36 (Step 12). The therapy delivery system 36 (FIG. 5), which is not shown in detail, can comprise any medical device, apparatus, or combination thereof configured to deliver a therapy signal to a nerve structure or nervous tissue of the ANS. The therapy delivery system 36 can include at least one electrode that is in electrical communication with a power source (not shown). The power source can include a battery or generator, such as a pulse generator operatively connected to an electrode. Alternatively, power may be supplied to the therapy delivery system 36 via biological energy harvesting. The power source may be positioned in any suitable location, such as integrated as part of the therapy delivery system, adjacent an electrode, at a remote site in or on the subject's body, and/or away from the subject's body in a remote location. One type of power source can include an implantable generator, which may be analogous to a cardiac pacemaker. In one example, one or more electrodes of the therapy delivery system 36 can be indirectly (e.g., wirelessly) connected to the power source.

In some instances, the therapy delivery system 36 can include a drug port (not shown) or other fluid conveying mechanism for delivering at least one pharmacological agent and/or biological agent to the target location. The drug port or other fluid conveying mechanism can be fluidly connected to a reservoir (not shown), which may be implanted within or located remotely from the subject. Any one or combination of pharmacological and/or biological agents can be deliverable to the target location. In some instances, the pharmacological and/or biological agent can include an agent, molecule, cell, compound, or the like capable of modulating ANS activity. In other instances, the pharmacological and/or biological agent can include an agent, molecule, cell, compound, or the like capable of preventing or treating a microbial infection (e.g., an anti-inflammatory agent). In other instances, the pharmacological agent and/or biological agent can be linked to a surface of the therapy delivery system 36 (e.g., one or more surfaces of an electrode), embedded and released from within polymer materials, such as a polymer matrix, or surrounded by and released through a carrier.

In one example, the therapy delivery system 36 can include an implantable neurostimulator. In some instances, the neurostimulator can include a controller (not shown) operably connected to an electrical lead (not shown) having at least one electrode (not shown) connected thereto. The electrode(s) comprising the neurostimulator can be monopolar, bipolar, or multipolar, and can operate as a cathode or an anode. The electrode(s) can be comprised of one or more electrically conductive materials, such as activated iridium, rhodium, titanium, platinum, or a combination thereof. All or only a portion of the electrode(s) may be coated with a thin surface layer of iridium oxide, titanium nitride, or other surface modifications to enhance electrical sensitivity.

The electrical lead can comprise carbon, doped silicon, or silicon nitride. The electrical lead can also be provided with a biocompatible fabric collar or band (not shown) about the periphery of the electrode(s) to allow the electrical lead to be more readily sutured or glued into place. Additionally, the controller can include a fixation plate (e.g., made of titanium) that uses standard anterior craniofacial screws to permit attachment of the neurostimulator to a bony structure (or structures) surrounding the PPF 18, for example.

The controller can be used to operate and/or supply power to the electrode(s). The controller may be powered by the power source. Where the therapy delivery system 36 includes a stimulation lead, the controller may change power output to the electrode(s) by way of polarity, pulse width, amplitude, frequency, voltage, current, and/or waveform. Where the therapy delivery system 36 comprises a drug port, the controller may change its output such that a pump, pressure source, or proportionally controlled orifice increases or decreases the rate at which a pharmacological and/or biological agent is/are delivered to the target location.

The controller may operate any number or combination of electrodes and/or fluid delivery mechanism. For example, the controller may be connected to stimulation leads and a peristaltic pump for delivering electric current and a pharmacological and/or biological agent to the target location. The controller may be entirely implanted within the subject or, alternatively, positioned externally about the subject (e.g., by leads).

Where the controller enables delivery of a electric current to the target location, the electric current may be episodic, continuous, phasic, in clusters, intermittent, upon demand by the subject or medical personnel, or pre-programmed to respond to a sensor (not shown) (e.g., a closed-loop system). The electrical signal can be operated at a constant voltage (e.g., at about 0.1 v to about 25 v), at a constant current (e.g., at about 0.1 microampes to about 5 milliamps), at a constant frequency (e.g., at about 1 Hz to about 10,000 Hz), and at a constant pulse-width (e.g., at about 10 μsec to about 2,000 μsec). Application of electric current can be monopolar, bipolar, or multipolar, depending upon the polarity of the electrode(s). The waveform(s) may be biphasic, square wave, sine wave, or other electrically safe and feasible combinations.

Where the controller enables delivery of a pharmacological and/or biological agent to the target location, the pharmacological and/or biological agent(s) may be delivered to the target location prior to, concurrent with, subsequent to, or instead of electric current. The pharmacological and/or biological agent(s) may be a neurotransmitter mimetic, neuropeptide, hormone, pro-hormone, antagonist, agonist, reuptake inhibitor or degrading enzyme thereof, peptide, protein, chemical agent, amino acid, nucleic acid, stem cell, or any combination thereof, and may be delivered by a slow release matrix or drug pump. Delivery of the pharmacological and/or biological agent(s) may be continuous, intermittent, chronic, phasic or episodic.

The therapy delivery system 36 can be part of an open-loop or closed-loop system. In an open-loop system, for example, a physician or subject may, at any time, manually or by the use of pumps, motorized elements, etc. adjust treatment parameters, such as pulse amplitude, pulse width, pulse frequency, or duty cycle of an electric current. Thus, in an open-loop system, therapy can be delivered on-demand. Alternatively, in a closed-loop system, treatment parameters (e.g., electric current) may be automatically (e.g., continuously) adjusted in response to a sensed physiological parameter (e.g., a symptom) or a related physiological parameter indicative of the extent of the chronic or refractory rhinitis being treated. For example, changes in inflammatory cells (such as eosinophils, neutrophils, macrophages or lymphocytes), proteins, cytokines, chemokines, intraluminal gases, histamine, leukotrienes, nitric oxide (and its synthases and metabolites), or other markers/constituents of innate or adaptive mucosal or systemic immunity may be monitored/detected and the system may be adjusted to address these changes. Also, changes in temperature, pH, mucosal edema, changes related to mucosal remodeling (e.g., basement membrane thickness, epithelial damage), venous congestion, blood flow, mucosal hydration and rhinorrhea may be monitored or detected.

In other instances, physiological parameters can include locoregional or systemic conditions or changes, such as other gross or molecular changes characteristic of chronic or refractory rhinitis. Example of such molecular changes can include up-regulation and/or down-regulation of various proteins (or their receptors). Such proteins may include, but are not limited to: interferon-alpha; interferon-gamma; interleukins (IL), such as IL-1-beta, IL-2, IL3-, IL-4, IL-5, IL-6, IL-7, IL-8, IL-10, IL-13, IL-15 and IL-17; growth-related oncogene-alpha; epithelial cell-derived neutrophil attractant-78; granulocyte chemotactic protein-2; eotaxin; released upon activation T-cell secreted (RANTES); thymus and activation-regulated chemokine (TARC), matrix metalloproteinases; vascular cell adhesion molecule-1; tumor necrosis factor-alpha; transforming growth factor-beta; chemokines (such as CCL13, CCL2, CCL8, CCL11, CCL18, CCL22, CXCL13); immunoglobulins; toll-like receptors; G-CSF; GM-CSF; MIP-1; VEGF; EGF; HGF; or other protein markers of inflammation.

In addition, the inflammatory cell profile of the nasal mucosa may be monitored. For instance, relative or absolute eosinophil, neutrophil, macrophage, or lymphocyte (Th1, Th2, Th17) counts may be determined. Alterations in dendritic cells or associated proteins may also be used. Other markers may include nitric oxide and/or its synthases or metabolites, oxygen tension, and markers of ciliary dysfunction or defects in mucociliary flow. Microbes and/or their byproducts may also be used as markers. For example, bacteria such *Staphylococcus aureus* or *Pseudomonas aeruginosa*, fungi, or viruses as well as by-products of these or other organisms may be used. Additionally, gene transcripts, protein markers, or markers of microbial biofilms may be used.

In a closed-loop feedback system, one or more sensors 40 (FIG. 5) configured to detect at least one physiological parameter associated with chronic or refractory rhinitis can be utilized. More detailed descriptions of sensors 40 that may be employed in a closed-loop system, as well as other examples of sensors and feedback control techniques that may be employed are disclosed in U.S. Pat. No. 5,716,377, which is hereby incorporated by reference in its entirety.

Figure 4:
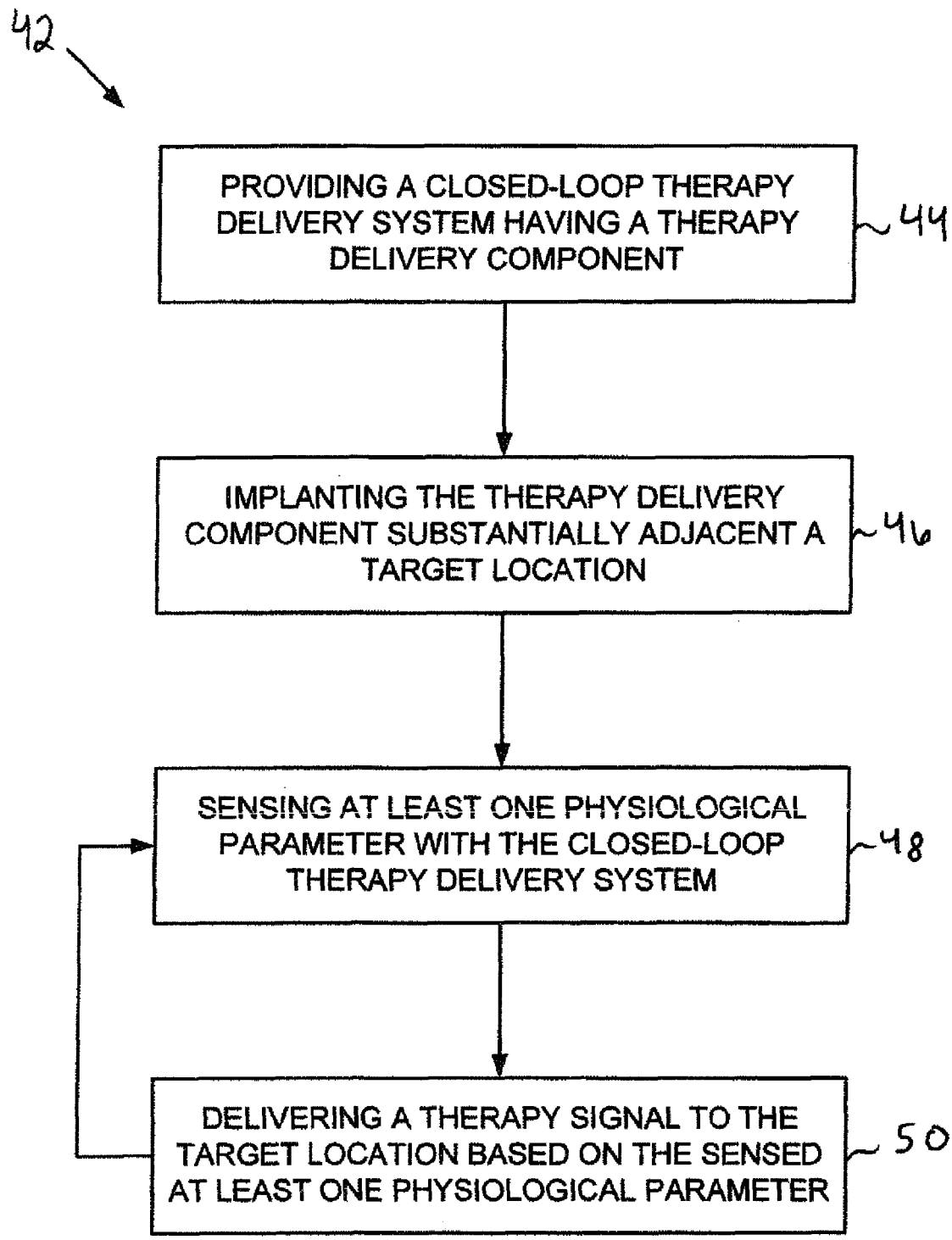
FIG. 4 is a process flow diagram illustrating a method for treating chronic or refractory rhinitis according to another aspect of the present disclosure.

Although described in more detail below, it should be appreciated that incorporating the therapy delivery system 36 as part of a closed-loop method 42 for treating chronic or refractory rhinitis can include the following steps (FIG. 4): providing a closed-loop therapy delivery system 36 having a therapy delivery component 38 (Step 44); implanting the therapy delivery component substantially a target location (Step 46); sensing at least one physiological parameter (Step 48) associated with chronic or refractory rhinitis; and delivering a therapy signal to the target location based on the sensed physiological parameter(s) (Step 50).

Physiological parameters detectable by the method 42 can include any characteristic, symptom, molecule, or function of the body that is associated with chronic or refractory rhinitis. Examples of such physiological parameters can include, but are not limited to, mucosal blood flow, mucosal thickness, mucosal secretion, protein or chemical concentrations (e.g., cytokines, histamines), pressure (e.g., nasal intraluminal pressure), nasal airflow (e.g., as a marker of congestion), drainage, electrochemical gradients, microbial products and byproducts, gases (e.g., nitric oxide), as well as other locoregional or systemic conditions or changes, such as other gross or molecular changes characteristic of chronic or refractory rhinitis.

Another aspect of the present disclosure can include implanting the therapy delivery system 36 in the subject so that at least one therapy delivery component 38 (e.g., an electrode) is positioned substantially adjacent the target location and is in electrical communication with one or more nerve structure(s) or nervous tissue(s) associated with the PPF 18. Alternatively, the therapy delivery system 36 can be implanted in the subject so that at least one therapy delivery component 38 (e.g., an electrode) is positioned directly adjacent the target location and in electrical communication with one or more nerve structure(s) or nervous tissue(s) associated with the PPF 18. In certain aspects, the target location can include at least one of the SPG 20, a greater palatine nerve (not shown in detail), a lesser palatine nerve (not shown in detail), a sphenopalatine nerve 32, a communicating branch between a maxillary nerve 34 and an SPG, an otic ganglion (not shown), an afferent fiber going into the otic ganglion, an efferent fiber going out of the otic ganglion, an infraorbital nerve (not shown), a vidian nerve 28, a greater superficial petrosal nerve 26, a lesser deep petrosal nerve 26, a trigeminal nerve (not shown), a posterior inferior lateral nasal branch (not shown) of the maxillary nerve, a anterior superior alveolar nerve (not shown), a nasopalatine nerve (not shown), an infraorbital nerve (not shown), a posterior superior alveolar nerve (not shown), an anterior ethmoidal nerve and its branches (e.g., a medial internal nasal branch, and a lateral internal nasal branch, an external nasal branch), as well as any other nerve, branch, or tributary of the other nerves comprising the ANS (discussed above).

In some instances, the therapy delivery component 38 is placed within the PPF 18 or, more specifically, in very close proximity to a nerve structure or nervous tissue associated with the PPF. In one example, the nerve structure or nervous tissue includes at least one of the SPG 20, the vidian nerve 28, or the sphenopalatine nerves 32. In other instances, the nerve structure or nervous tissue includes the SPG 20.

The therapy delivery system 36, and in particular the therapy delivery component 38, can be delivered to and implanted at the target location via any one or combination of surgical approaches. In some instances, the therapy delivery system 36 can be implanted substantially adjacent a target location where modulation of the SNS is effective to treat chronic or refractory rhinitis. In other instances, the therapy delivery system 36 can be implanted substantially adjacent a target location where modulation of the PNS is effective to treat chronic or refractory rhinitis. In other aspects, the therapy delivery system 36 can be implanted substantially adjacent a target location where modulation of the SNS and the PNS is effective to treat chronic or refractory rhinitis.

In other aspects, the therapy delivery system 36 can be delivered to the target location through the greater palatine canal via a trans-palatal approach as disclosed in U.S. Patent Publication No. 2010/0049230 A1 to Benary et al., the entirety of which is hereby incorporated by reference. In other instances, the therapy delivery system 36 can be delivered to the target location via a trans-nasal approach as disclosed in U.S. Patent Publication No. 2006/0195169 A1 to Gross et al., the entirety of which is hereby incorporated by reference. In another aspect, the therapy delivery system 36 can be delivered to the target location via a trans-coronoid notch approach as disclosed in U.S. Pat. No. 6,526,318 to Ansarinia, the entirety of which is hereby incorporated by reference. In other aspects, the therapy delivery system 36 can be delivered to the target location via a gingival-buccal approach as disclosed in U.S. Patent Publication No. 2010/0185258 A1 to Papay, the entirety of which is hereby incorporated by reference. It will be appreciated that any of the foregoing surgical procedures, as well as any other suitable percutaneous, laparoscopic, or open surgical procedure may also be used to implant the therapy delivery system 36.

Where the therapy delivery system 36 is part of a closed-loop system, one or more sensors 40 can be placed or implanted in the subject to allow detection of at least one physiological parameter associated with chronic or refractory rhinitis. In some instances, one or more sensors 40 can be implanted in the nasal passage or nasal cavity of the subject. For example, one or more sensors 40 can be securely affixed to the mucous membrane lining a portion of the nasal passage or nasal cavity. In other instances, one or more sensors 40 can be securely affixed within one or both of the nares (e.g., to detect nasal airflow).

Figure 5:
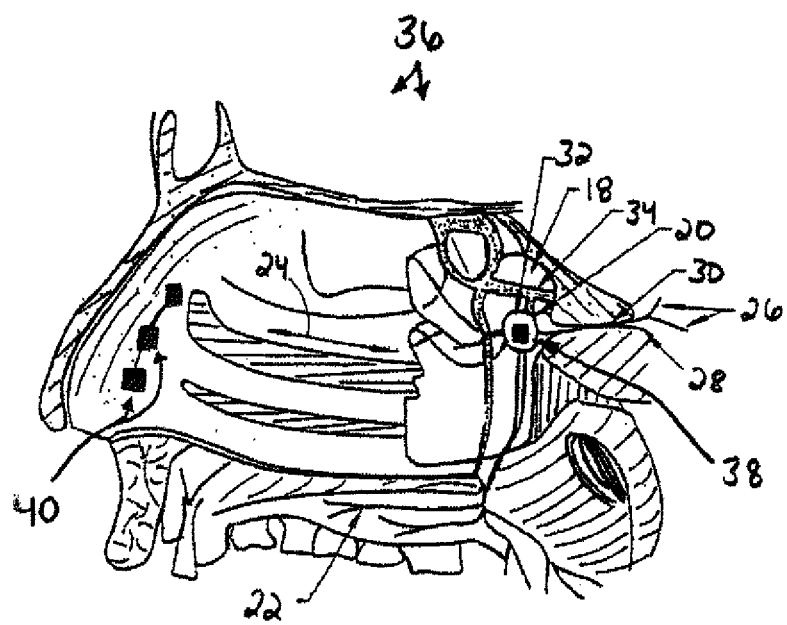
FIG. 5 is a schematic illustration showing an implanted closed-loop therapy delivery system in accordance with another aspect of the present disclosure.

The sensor(s) 40 can be arranged in any suitable configuration. In some instances, only a single sensor 40 can be implanted. In other instances, two or more sensors 40 can be implanted. In one example, a sensor array comprising three sensors 40 can be implanted in a nasal passage of the subject (FIG. 5). Where a sensor array is used, different sensors 40 can detect different physiological parameters. Alternatively, two or more sensors 40 comprising a sensor array can each detect the same physiological parameter, albeit at a different concentration. A sensor array can be configured in series, as shown in FIG. 5, or in any other configuration to facilitate detection of one or more physiological parameters associated with chronic or refractory rhinitis.

In another aspect, the therapy delivery system 36 (e.g., the therapy delivery component 38) can be activated to deliver a therapy signal (e.g., electric current) to the target location following implantation of the therapy delivery system. The ANS controls blood supply into the nasal mucosa and the secretion of mucus. The diameter of the resistance vessels in the nose is mediated by the SNS, while the PNS controls glandular secretion and, to a lesser extent, exerts an effect on the capacitance vessels. Either a hypoactive SNS or a hyperactive PNS can engorge these vessels, creating an increased swelling of the nasal mucosa and ultimately congestion. Additionally, activation of the PNS can increase mucosal secretions leading to excess runny nose.

In one aspect, a therapy signal (e.g., electric current) can be delivered to a target location, such as the SPG 20 and/or the vidian nerve 28 to effectively block or reduce parasympathetic activity. Blocking or reduction of parasympathetic activity can decrease or alleviate at least one symptom associated with chronic or refractory rhinitis, such as swelling of nasal mucosa and mucosal secretion. For example, blocking or reduction of parasympathetic activity can cause decreased swelling of the nasal mucosa, which results in decreased nasal blockage and, thus, normal drainage. It will be appreciated that delivery of a therapy signal to a parasympathetic nerve structure can block or inhibit efferent and/or afferent neuronal activity thereof as well.

In another aspect, a therapy signal (e.g., electric current) can be delivered (e.g., selectively delivered) to a target location, such as the sympathetic fibers comprising the SPG 20 to substantially activate or increase sympathetic activity. Activating or increasing sympathetic activity can decrease or alleviate at least one symptom associated with chronic or refractory rhinitis, such as mucosal blood flow and mucosal thickness. For example, activating or increasing sympathetic activity can promote arterial vasoconstriction, thereby reducing mucosal blood flow and mucosal thickness, in addition to restoring nasal patency. It will be appreciated that delivery of a therapy signal to a sympathetic nerve structure can increase or activate efferent and/or afferent neuronal activity thereof as well.

In other instances, it will be appreciated that one or more therapy signals can be concurrently or intermittently delivered to both sympathetic and parasympathetic nerve structures. For example, a first therapy signal can be delivered to a sympathetic nerve structure to activate or increase sympathetic activity, while a second therapy signal can be delivered to a parasympathetic nerve structure to decrease or block parasympathetic activity.

In a further aspect (FIG. 4), a therapy signal (e.g., electric current) can be delivered to a target location, such as the SPG 20 (as described above). In a closed-loop configuration, one or more sensors 40 located in the nasal cavity of the subject can then detect at least one physiological parameter associated with chronic or refractory rhinitis, such as mucosal blood flow or mucosal secretion. The therapy delivery component 38 (e.g., an electrode) can be activated to deliver a therapy signal, such as electric current to the target location. Where electric current is delivered to the SPG 20 (e.g., to block or decrease parasympathetic activity), the amount or volume of nasal secretions may decrease as a result. The implanted sensor(s) 40 can then detect the decreased amount or volume of nasal secretions. Based on the detected amount or volume of nasal secretions, the therapy delivery system 36 can adjust the therapy signal accordingly. For instance, a controller of the therapy delivery system 36 can cease delivery of therapy signals to the target location when the detected amount or volume of nasal secretions has reached a normal or healthy level.

Although the ultimate goal of eradicating chronic or refractory rhinitis remains, symptom reduction is a major goal in subjects with chronic or refractory rhinitis. Advantageously, the present disclosure provides methods for assisting with, or replacing, current standard treatments in subjects with chronic or refractory rhinitis whose symptoms are recalcitrant to such standard treatments. Unlike conventional treatments that often take months or years to achieve efficacy, the therapeutic methods of the present disclosure can provide symptom relief immediately after implementation. By providing both open- and closed-loop therapy delivery systems, the present disclosure permits both on-demand or continuous monitoring and treatment of symptoms associated with chronic or refractory rhinitis, without systemic side effects, while also delivering therapy on an as-needed basis to improve patients' quality of life.

Another aspect of the present disclosure includes a method 52 (FIG. 6) for moistening at least one nasal passage of a subject. The method 52 can be employed to treat conditions such as rhinitis sicca or other conditions leading to dryness of the nasal cavity. As shown in FIG. 6, the method 52 can include the steps of: providing a therapy delivery system 36 having a therapy delivery component 38 (Step 52); implanting the therapy delivery system (e.g., the therapy delivery component) substantially adjacent a target location (Step 54); and activating the therapy delivery component to deliver a therapy signal to the target location and thereby moisten the nasal cavity of the subject (Step 56). Except as described below, the method 52 can be identically performed as the methods 10 and 42 described above. For example, the method 52 can be implemented as part of an open-loop or closed-loop system.

The nose is instrumental in providing moist air to the lungs. The lungs are composed of very delicate membranes that exchange oxygen into the blood stream and allow carbon dioxide from the blood to pass back into the air so it can leave the body. To do that, the lung membranes must be moist. Dry membranes cannot dissolve these gases. Since dry air in the lungs would dry out the lung membranes, the body must moisten air as it is inspired. The nose is the primary mechanism for doing so.

The nose includes several outcroppings, which are referred to as turbinates. The turbinates are long, 3- to 4-inch ridges that protrude into the nasal airway. They are lined by an elastic and moist membrane that constantly secretes mucous and water. This moisture evaporates into the incoming dry air, which is moisturized and passed into the lungs. Ideally, the nose does not have to work especially hard if the air is already humidified. In addition, any dust, dirt, pollen, bacteria, or viruses are filtered out of the air and adhere to the turbinates as the turbinates are moist and sticky due to secreted mucous. Such debris is typically trapped by the mucous.

The nose is covered with fine small hairs (called cilia) that constantly push the mucous to the back of the nose. The mucous then drains down the back of the nose, which is swallowed and digested in the stomach. The cilia typically function best at a humidity level of about 50%. If the humidity level is less than 50%, the cilia may slow down and thereby cause the mucous to thicken and accumulate.

The nose tries to mitigate dry mucous build-up and excessive drying of the mucosal lining by causing the turbinates to swell, which temporarily closes the nasal air passage. This allows the membranes to be cleaned and remoisturized. This occurs to a more minor degree on a daily basis during "nasal cycling". If the humidity is over 50%, most people never notice temporary blockage of the nose as the turbinates only swell moderately. Some people with a nasal passage way obstruction (e.g., a deviated nasal septum, nasal polyps, or a thin nose anatomy), however, become totally blocked during normal "nasal cycling". If the humidity is less than 50%, the turbinates can swell and cause severe nasal congestion in such patients.

Moreover, nasal dryness is often the first step in a cascade of events that can lead to chronic nasal congestion, nose bleeds, and sinusitis. Prolonged nasal dryness can eventually cause the nose dry out, thereby increasing mucosal thickness and providing an ideal target for infection. In other instances, prolonged nasal dryness can cause the nasal mucosal to crack and fissure. If a blood vessel is located at the crack or fissure, it will cause bleeding (epistaxis). Thus, in certain aspects of the present disclosure, the method 52 can increase the moisture content in at least one nasal passage of a subject suffering from nasal dryness (e.g., prolonged or chronic nasal dryness). The nasal dryness can be caused by any one or combination of factors, including a deviated nasal septum, nasal polyps, a thin nose anatomy, infection, and various medical interventions or procedures. For example, turbinectomy can lead to empty nose syndrome.

In one aspect of the method 52, a therapy delivery system 36 can be provided at Step 52. The therapy delivery system 36 can be similarly or identically configured as the therapy delivery system described above. For example, the therapy delivery system 36 can comprise any medical device, apparatus, or combination thereof configured to deliver a therapy signal to a nerve structure or nervous tissue of the ANS. The therapy delivery system 36 can include a therapy delivery component 38 configured to deliver a therapy signal to a target location. In one example, the therapy delivery component 38 can include an electrode in electrical communication with a power source. As discussed above, the therapy delivery component 38 can additionally or optionally included a drug port or fluid delivery mechanism for delivering a pharmacological agent and/or biological to the target location.

At Step 54, the therapy delivery system 36 can be implanted in the subject so that at least one therapy delivery component 38 of the system is positioned substantially adjacent a target location where modulation of the ANS is effective to moisten the nasal passage. The therapy delivery system 36 can be implanted in an identical or similar manner as described above. For example, the therapy delivery system 36 can be implanted substantially adjacent a target location where modulation of the SNS is effective to moisten at least one nasal passage. In other instances, the therapy delivery system 36 can be implanted substantially adjacent a target location where modulation of the PNS is effective to moisten at least one nasal passage. In other aspects, the therapy delivery system 36 can be implanted substantially adjacent a target location where modulation of the SNS and the PNS is effective to moisten at least one nasal passage.

In another aspect of the method 52, the therapy delivery system 36 (e.g., the therapy delivery component 38) can be activated to deliver a therapy signal (e.g., electric current) to the target location following implantation of the therapy delivery system. For example, a therapy signal (e.g., electric current) can be delivered to a target location, such as the vidian nerve 28 to effectively increase or activate parasympathetic activity. Activating or increasing parasympathetic activity can treat or alleviate at least one symptom associated with nasal dryness by causing the nasal mucosa and/or mucosal secretion to swell, thereby increasing the overall moisture content of all or only a portion of the nasal passage(s). It will be appreciated that delivery of a therapy signal to a parasympathetic nerve structure can activate or increase efferent and/or afferent neuronal activity thereof as well.

In another aspect, a therapy signal (e.g., electric current) can be delivered (e.g., selectively delivered) to a target location, such as the sympathetic fibers comprising the SPG 20 to substantially block or decrease sympathetic activity. Blocking or decreasing sympathetic activity can treat or alleviate at least one symptom associated with nasal dryness by increasing mucosal blood flow. For example, blocking or decreasing sympathetic activity can promote arterial vasorelaxation, thereby increasing mucosal blood flow and mucosal thickness to a normal or healthy level. It will be appreciated that delivery of a therapy signal to a sympathetic nerve structure can block or decrease efferent and/or afferent neuronal activity thereof as well.

In other instances, it will be appreciated that one or more therapy signals can be concurrently or intermittently delivered to both sympathetic and parasympathetic nerve structures. For example, a first therapy signal can be delivered to a sympathetic nerve structure to block or decrease sympathetic activity, while a second therapy signal can be delivered to a parasympathetic nerve structure to activate or increase parasympathetic activity.

In a further aspect, a therapy signal (e.g., electric current) can be delivered to a target location (e.g., the SPG 20) as part of a closed-loop system (as described above). In a closed-loop configuration, one or more sensors 40 located in the nasal cavity of the subject can detect at least one physiological parameter associated with nasal dryness. The therapy delivery component 38 (e.g., an electrode) can then be activated to deliver a therapy signal, such as electric current to the target location. Where electric current is delivered to the SPG 20 (e.g., to increase or activate parasympathetic activity), the amount or volume of nasal secretions may increase as a result. The implanted sensor(s) 40 can then detect the increased amount or volume of nasal secretions. Based on the detected amount or volume of nasal secretions, the therapy delivery system 36 can adjust the therapy signal accordingly. For instance, a controller of the therapy delivery system 36 can increase delivery of therapy signals to the target location until the detected amount or volume of nasal secretions has reached a normal or healthy level.

From the above description, those skilled in the art will perceive improvements, changes and modifications. For example, it will be appreciated that the therapy delivery system can be configured to deliver transcutaneous therapy (e.g., electric current) using, for example, magnetic wave therapy as disclosed in U.S. Provisional Patent Application Ser. No. 61/778,521, filed Mar. 13, 2013, the entirety of which is hereby incorporated by reference. Such improvements, changes, and modifications are within the skill of one in the art and are intended to be covered by the appended claims.

The following is claimed:

1. A method for treating chronic or refractory rhinitis in a subject, said method comprising the steps of:
    implanting a therapy delivery system in the subject so that at least one therapy delivery component of the system is positioned substantially adjacent a target location where modulation of the autonomic nervous system (ANS) is effective to treat chronic or refractory rhinitis in a subject suffering therefrom, the therapy delivery component including at least one electrode configured to deliver electric current to the target location; and
    delivering electric current to the at least one electrode to effect a change in the ANS to treat the chronic or refractory rhinitis in the subject.

2. The method of claim 1, wherein the target location is a nerve structure associated with the pterygopalatine fossa (PPF).

3. The method of claim 2, wherein the nerve structure includes at least one of a sphenopalatine ganglion (SPG), a vidian nerve, or a sphenopalatine nerve.

4. The method of claim 2, wherein delivery of electric current to the at least one electrode modulates afferent neuronal activity.

5. The method of claim 2, wherein delivery of electric current t the at least one electrode modulates efferent neuronal activity.

6. The method of claim 1, wherein modulation of the ANS is effective to alter at least one of mucosal blood flow, mucosal thickness, and mucosal secretion.

7. The method of claim 1, wherein said step of implanting the therapy delivery system includes positioning the therapy delivery component substantially adjacent a target location where modulation of the parasympathetic nervous system (PNS) and/or the sympathetic nervous system (SNS) is effective to treat chronic or refractory rhinitis.

8. The method of claim 7, wherein modulation of the PNS comprises substantially blocking or reducing parasympathetic activity.

9. The method of claim 8, wherein substantially blocking or reducing parasympathetic activity decreases at least one of swelling of nasal mucosa and mucosal secretion.

10. The method of claim 7, wherein modulation of the SNS comprises substantially activating or increasing sympathetic activity.

11. The method of claim 10, wherein substantially activating or increasing sympathetic activity decreases at least one of mucosal blood flow, and mucosal thickness.

* * * * *